US011471609B2

United States Patent
Holmqvist

(10) Patent No.: US 11,471,609 B2
(45) Date of Patent: Oct. 18, 2022

(54) ACTUATION MECHANISM FOR A MEDICAMENT DELIVERY DEVICE

(71) Applicant: SHL MEDICAL AG, Zug (CH)

(72) Inventor: Anders Holmqvist, Värmdo (SE)

(73) Assignee: SHL MEDICAL AG, Zug (CH)

( * ) Notice: Subject to any disclaimer, the term of this patent is extended or adjusted under 35 U.S.C. 154(b) by 303 days.

(21) Appl. No.: 16/312,905

(22) PCT Filed: Jun. 1, 2017

(86) PCT No.: PCT/EP2017/063392
§ 371 (c)(1),
(2) Date: Dec. 21, 2018

(87) PCT Pub. No.: WO2017/220311
PCT Pub. Date: Dec. 28, 2017

(65) Prior Publication Data
US 2020/0001014 A1    Jan. 2, 2020

(30) Foreign Application Priority Data

Jun. 23, 2016 (SE) .................... 1650905-1

(51) Int. Cl.
*A61M 5/315* (2006.01)
(52) U.S. Cl.
CPC ...... *A61M 5/3157* (2013.01); *A61M 5/31553* (2013.01); *A61M 5/31585* (2013.01); *A61M 2205/581* (2013.01)
(58) Field of Classification Search
CPC ............ A61M 5/3157; A61M 5/31595; A61M 5/31533; A61M 2205/581;
(Continued)

(56) References Cited

U.S. PATENT DOCUMENTS 5,851,079 A * 12/1998 Horstman .......... B65D 83/0011
401/172
9,358,341 B2    6/2016 Plumptre et al.
(Continued)

FOREIGN PATENT DOCUMENTS

CN      102648013 A    8/2012
CN      104640587 A    5/2015
(Continued)

*Primary Examiner* — Nilay J Shah
*Assistant Examiner* — Robert F Allen
(74) *Attorney, Agent, or Firm* — McDonnell Boehnen Hulbert & Berghoff LLP

(57) ABSTRACT

The present invention relates to a medicament delivery device comprising a housing, an actuation mechanism (40) arranged inside said housing, the actuation mechanism comprising a plunger rod (42) arranged to act on a stopper (18) of a medicament container (16); an actuator (84) arranged slidable and connected to the plunger rod (42) for acting on the stopper (18) when said actuator (84) is operated by displacing it in a longitudinal direction of the actuation mechanism (40); an activator (104) rotatably arranged for activating said actuation mechanism and for setting a dose; said activator (104) comprising a generally tubular activator sleeve (148), said activator sleeve (148) comprises protrusions (150) arranged to interact with ledges (90) on said actuator (84) such that said activator sleeve (148) is rotated when said actuator (84) is operated. The invention is characterised in a first audio generating mechanism comprising audio generating elements (94) and said protrusions (150), which protrusions (150) are arranged to cooperate with said audio generating elements (94) for generating an audible signal after said operation for delivering a dose.

8 Claims, 18 Drawing Sheets

(58) Field of Classification Search
CPC .......... A61M 5/31553; A61M 5/31585; A61M 2005/2411; A61M 2005/2418; A61M 2205/582; A61M 5/3156; A61M 5/31541
See application file for complete search history.

(56) References Cited

U.S. PATENT DOCUMENTS

| | | | |
|---|---|---|---|
| 2012/0123350 A1* | 5/2012 | Giambattista ....... | A61M 5/2033 604/198 |
| 2012/0283652 A1* | 11/2012 | MacDonald ........ | A61M 5/3146 604/211 |
| 2015/0238699 A1* | 8/2015 | Butler ................. | A61M 5/3158 604/228 |
| 2019/0192781 A1* | 6/2019 | Chuvashova ..... | A61M 5/31565 |

FOREIGN PATENT DOCUMENTS

| | | | |
|---|---|---|---|
| WO | 2011039206 A2 | 4/2011 | |
| WO | 2011039209 A1 | 4/2011 | |
| WO | 2011039233 A1 | 4/2011 | |
| WO | WO-2011039233 A1 * | 4/2011 | ........ A61M 5/31543 |
| WO | 2016001298 A1 | 1/2016 | |
| WO | 2016/055626 | 4/2016 | |

* cited by examiner

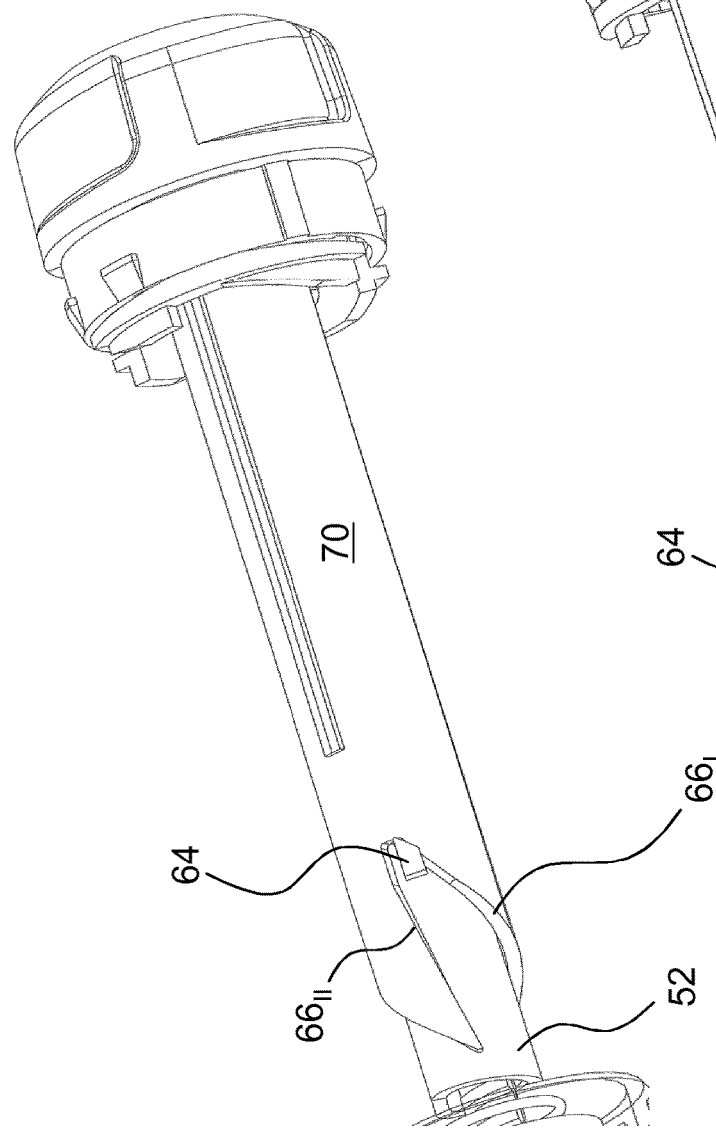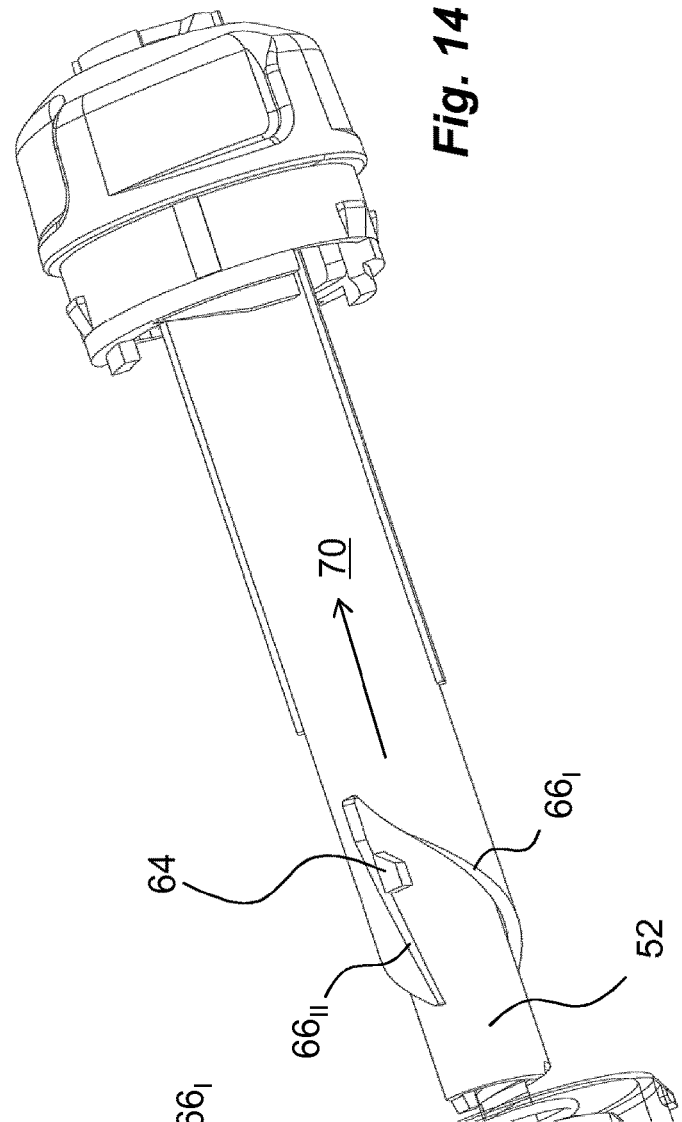

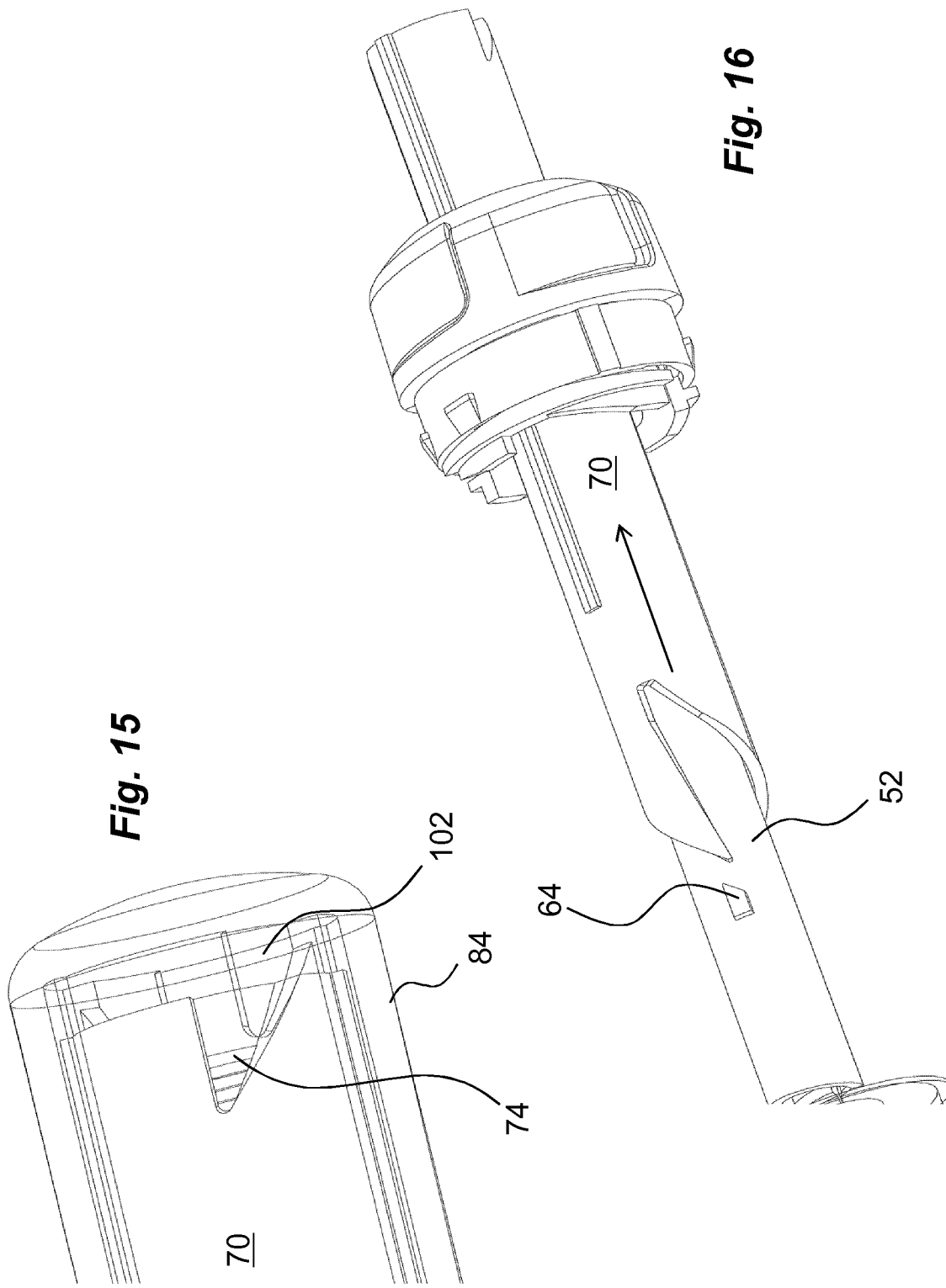

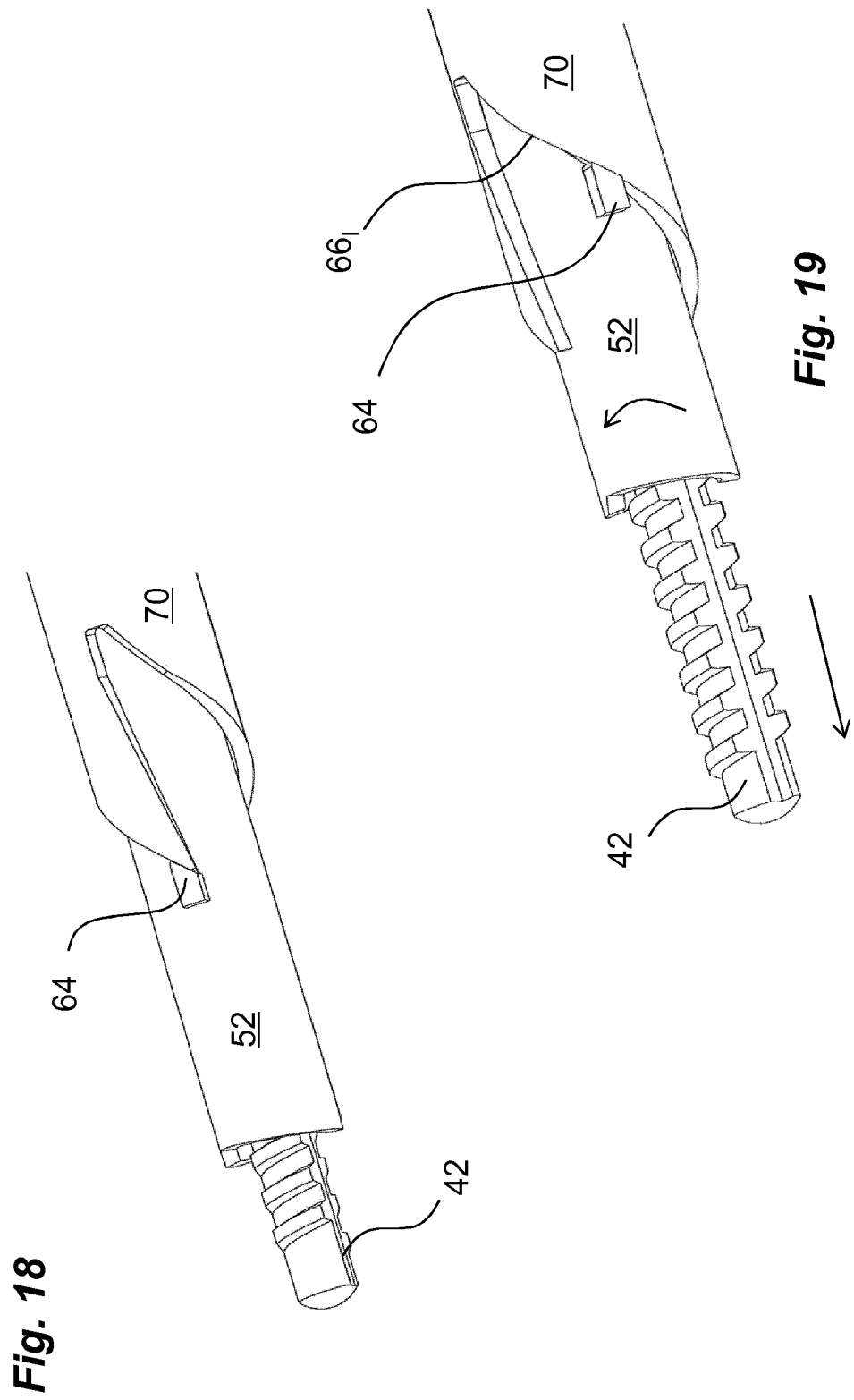

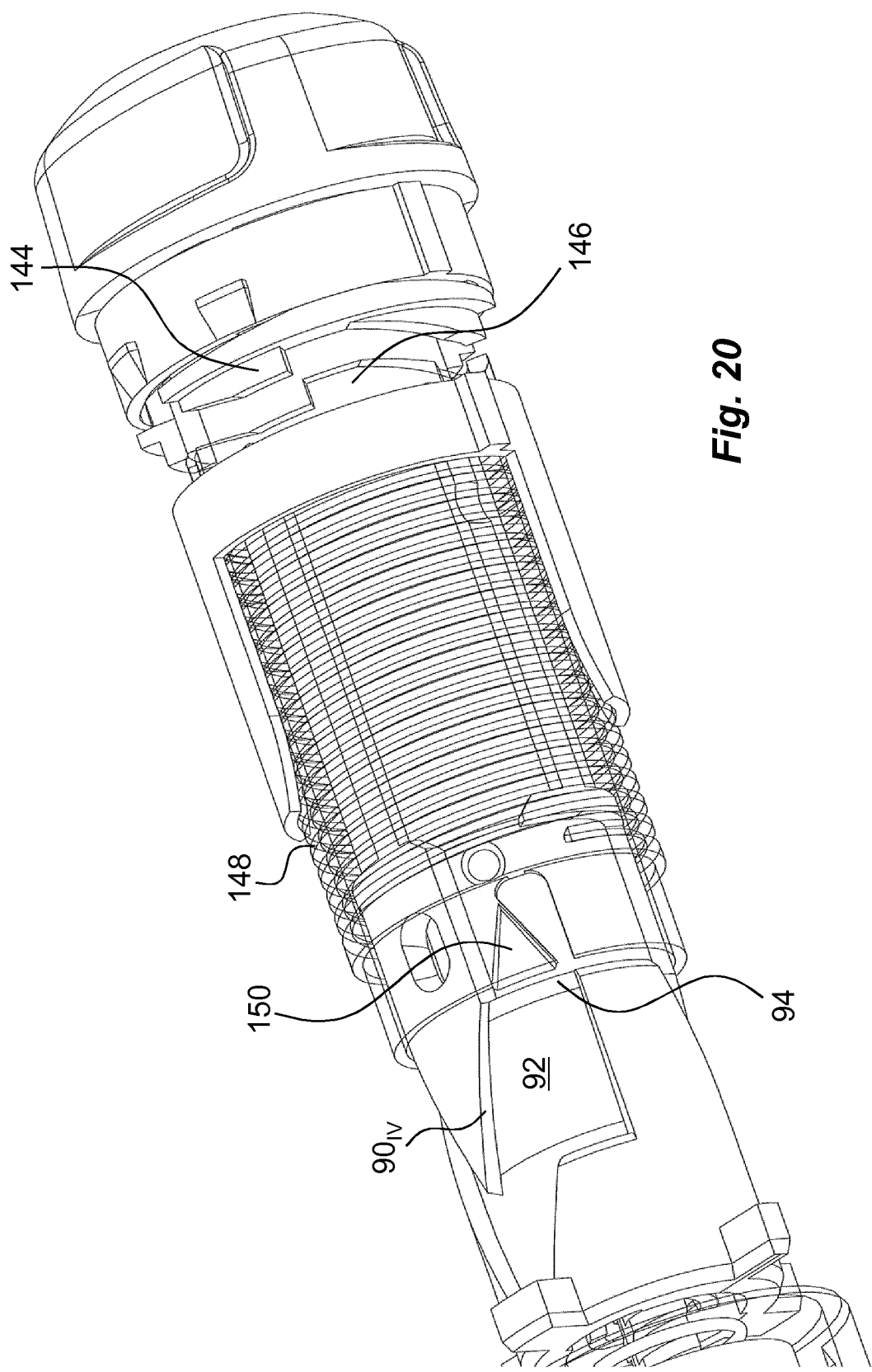

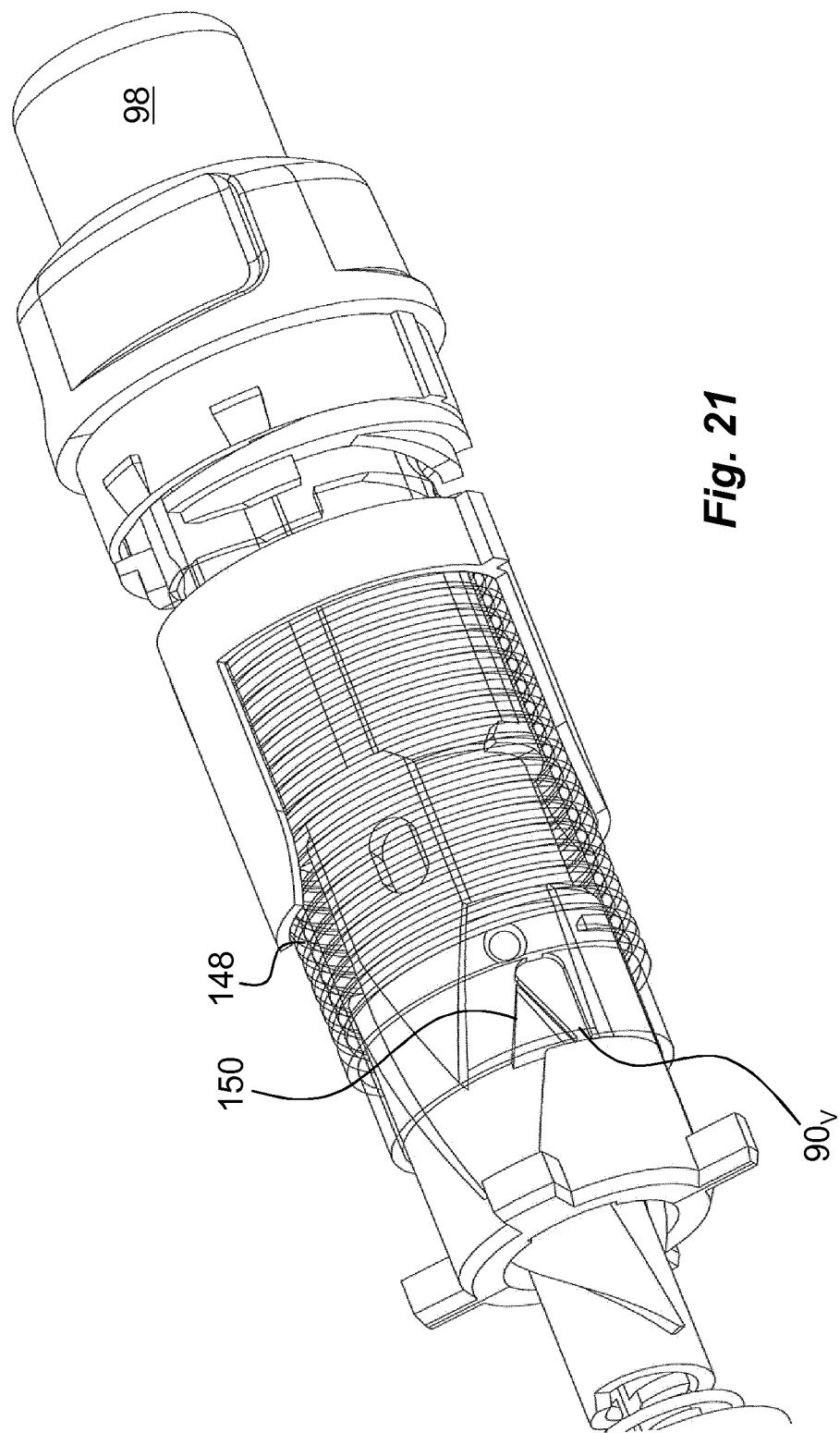

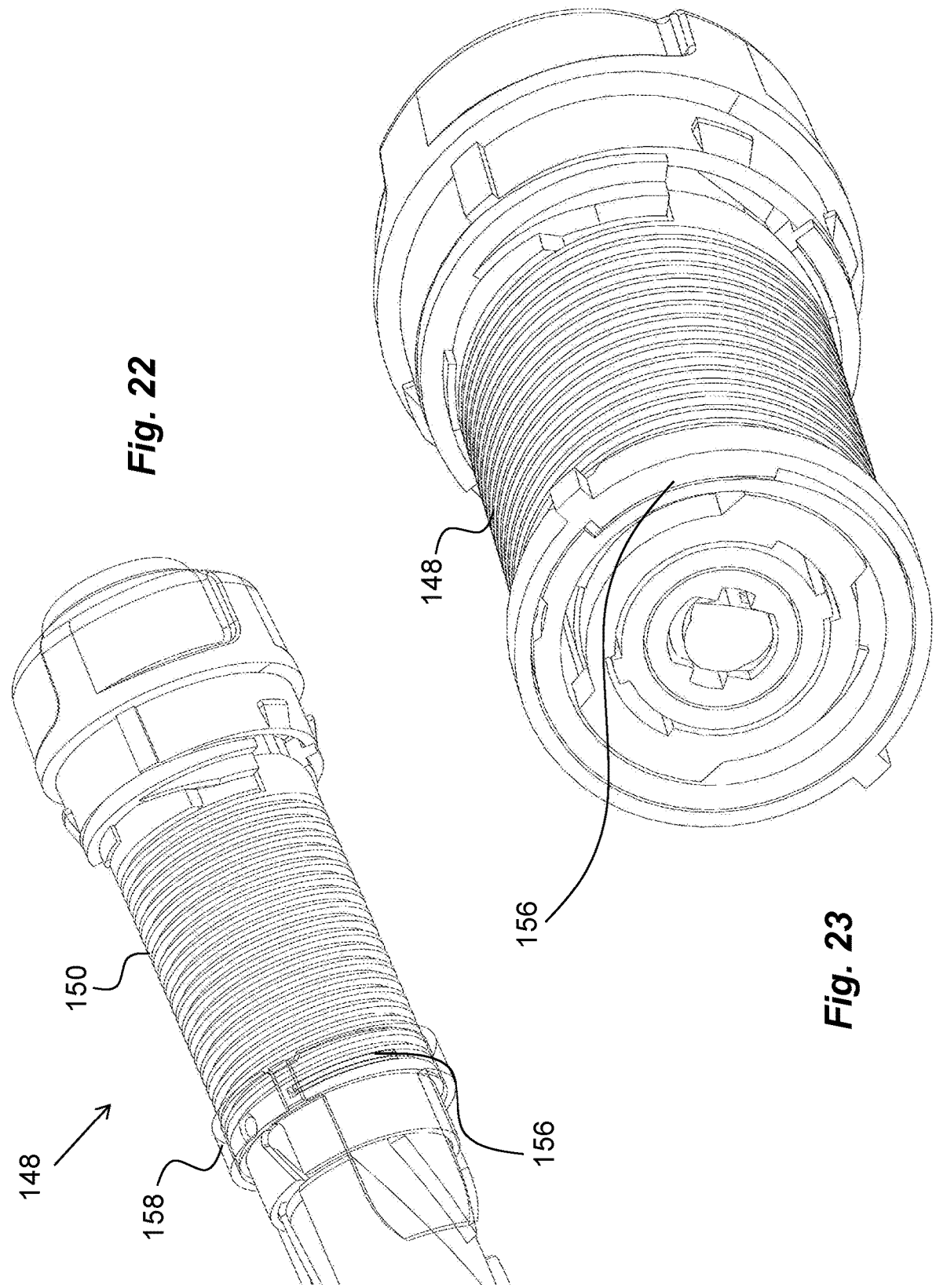

ACTUATION MECHANISM FOR A MEDICAMENT DELIVERY DEVICE

CROSS REFERENCE TO RELATED APPLICATIONS

The present application is a U.S. National Phase Application pursuant to 35 U.S.C. § 371 of International Application No. PCT/EP2017/063392 filed Jun. 1, 2017 which claims priority to Swedish Patent Application No. 1650905-1 filed Jun. 23, 2016. The entire disclosure contents of these applications are hereby incorporated by reference into the present application.

TECHNICAL AREA

The present invention relates to an actuation mechanism for a medicament delivery device and in particular a so called pen injector provided with a number of specific features.

BACKGROUND OF INVENTION

Many injectors on the market, especially pen-injectors, are provided with a functionality to allow multiple doses to be given from a medicament container. In many instances the dose quantity is fixed and is set just before a dose is to be delivered. Thus, a manual dose setting sequence is first performed and then a manual dose delivery sequence is performed. In many instances, since many users of these types of medicament delivery devices are inexperienced, it is often a desire that the user is provided with some sort of indication or information that a dose delivery sequence has been performed and that it is safe to remove the medicament delivery device from a dose delivery site.

Document US 2015/0238699 discloses such a medicament delivery device having a dose setting member that is operated before dose delivery. The dose setting member is operably connected to a drum via a peg on the dose setting member placed in a spirally extending groove on the drum. The drum is in turn operably connected to a nut via a ratchet, where the nut is threadedly connected to a plunger rod.

When setting a dose, the dose setting member is pulled distally a certain distance in relation to the housing, where the distance corresponds to the set dose quantity. The peg will then slide in the spiral groove which causes the drum to be rotated. Because of the design of the ratchet, the nut will not rotate with the drum.

When a dose is to be administered, the dose setting member is pushed manually in the proximal direction. The peg again slides in the spiral groove, whereby the drum is rotated in the opposite direction. Because of the design of the ratchet, the nut will also rotate, whereby the plunger rod is moved in the proximal direction, acting on a stopper of a medicament container such that the dose is expelled.

In order to provide information to a user regarding operation of the medicament delivery device, first and second feedback elements are arranged. The first feedback element is arranged as ribs on surfaces of the spiral groove of the drum. The second feedback element is the peg that runs in the spiral groove. Thus when the peg is moved in the groove it will ride over the ribs, causing a tactile or audible feedback to the user. The information is thus provided during dose setting and/or dose delivery sequence, depending on which surfaces of the groove that are provided with the ribs.

A drawback of the design of US 2015/0238699 is that the ribs have to be rather large in order to actually provide a tactile and audible feedback. However, such large ribs will adversely affect the function due to increased resistance between the peg and the groove. Further, some users may be confused and/or don't like when the medicament delivery device is making noises and vibrates during the entire dose delivery sequence.

BRIEF DESCRIPTION OF INVENTION

The aim of the present invention is to provide a reliable and simple solution of informing a user that a dose delivery sequence has been completed and that it is safe to remove the medicament delivery device.

This aim is solved with a medicament delivery device comprising the features of the independent patent claim. Preferable embodiments of the invention form the subject of the dependent patent claims.

According to a main aspect of the invention, it may comprise a medicament delivery device comprising a housing and an actuation mechanism arranged inside the housing. The actuation mechanism may comprise a plunger rod arranged to act on a stopper of a medicament container as well as an actuator arranged slidable and connected to the plunger rod for acting on the stopper when the actuator is operated by displacing it in a longitudinal direction of the actuation mechanism.

Further, an activator may be rotatably arranged for activating said actuation mechanism and for setting a dose, where the activator may comprise a generally tubular activator sleeve. The activator sleeve may comprise protrusions arranged to interact with ledges on the actuator such that the activator sleeve is rotated when the actuator is operated.

According to the invention, a first audio generating mechanism may be provided, comprising audio generating elements and the protrusions, wherein the protrusions are arranged to cooperate with the audio generating elements for generating an audible signal after the operation for delivering a dose. With this solution, components that perform dose delivery functions also act to generate information to a user. Thus no additional components or solutions are necessary.

According to an aspect of the invention, the first audio generating element may comprise surface areas on which the protrusions slide during rotation of the actuator sleeve, wherein the surfaces areas are arranged with first ledges causing sudden impact of the protrusions. Thus, a pure mechanical design solution is used to cause the audio information. According to one feasible solution, the surfaces areas are slanted and terminate in the first ledges.

Preferably the first ledges may also function as locking elements so as to lock the actuator after operation for delivering a dose of medicament. As stated above, components are used for several purposes and functions.

The actuator may be arranged with second ledges cooperating with the protrusions, which second ledges are arranged inclined in relation to the longitudinal direction, and preferably the first ledges are interconnected with the second ledges such that turning of the activator sleeve moves the protrusions from a locking position to a release position of the actuator.

The medicament delivery device may further comprise a toggle sleeve operably arranged between the actuator and the plunger rod for urging the plunger rod in a proximal direction during operation of the actuator, wherein said plunger rod is arranged with threads. A driver is non-rotatably connected to the plunger rod, wherein the driver is arranged with protrusions on its outer surface. Further, toggle sleeve is arranged with surfaces inclined in relation to the longitudinal direction, causing a rotation of the driver and the plunger rod when the actuator and the toggle sleeve are moved in the proximal direction.

According to the invention, the medicament delivery device may further comprise a second audio generating mechanism comprising audio generating elements arranged between the driver and a component fixed in relation to the housing. This solution provides a further means for informing a user that a dose delivery sequence has been performed. Again, no additional components have been used in order to provide the audio information.

According to one solution, the second audio generating elements comprise slanting surfaces ending in ledges causing sudden impact of said driver. Preferably the driver may be arranged with slanting surfaces on a proximal end surface and that the fixed component is arranged with mating slanting surfaces. Further, the fixed component may be a wall of the housing.

These and other aspects of, and advantages with, the present invention will become apparent from the following detailed description of the invention and from the accompanying drawings.

BRIEF DESCRIPTION OF DRAWINGS

In the following detailed description of the invention, reference will be made to the accompanying drawings, of which FIGS. 11-23 are detailed views with housing parts removed showing different functional stages of the medicament delivery device.

DETAILED DESCRIPTION OF THE INVENTION

Figure 1:
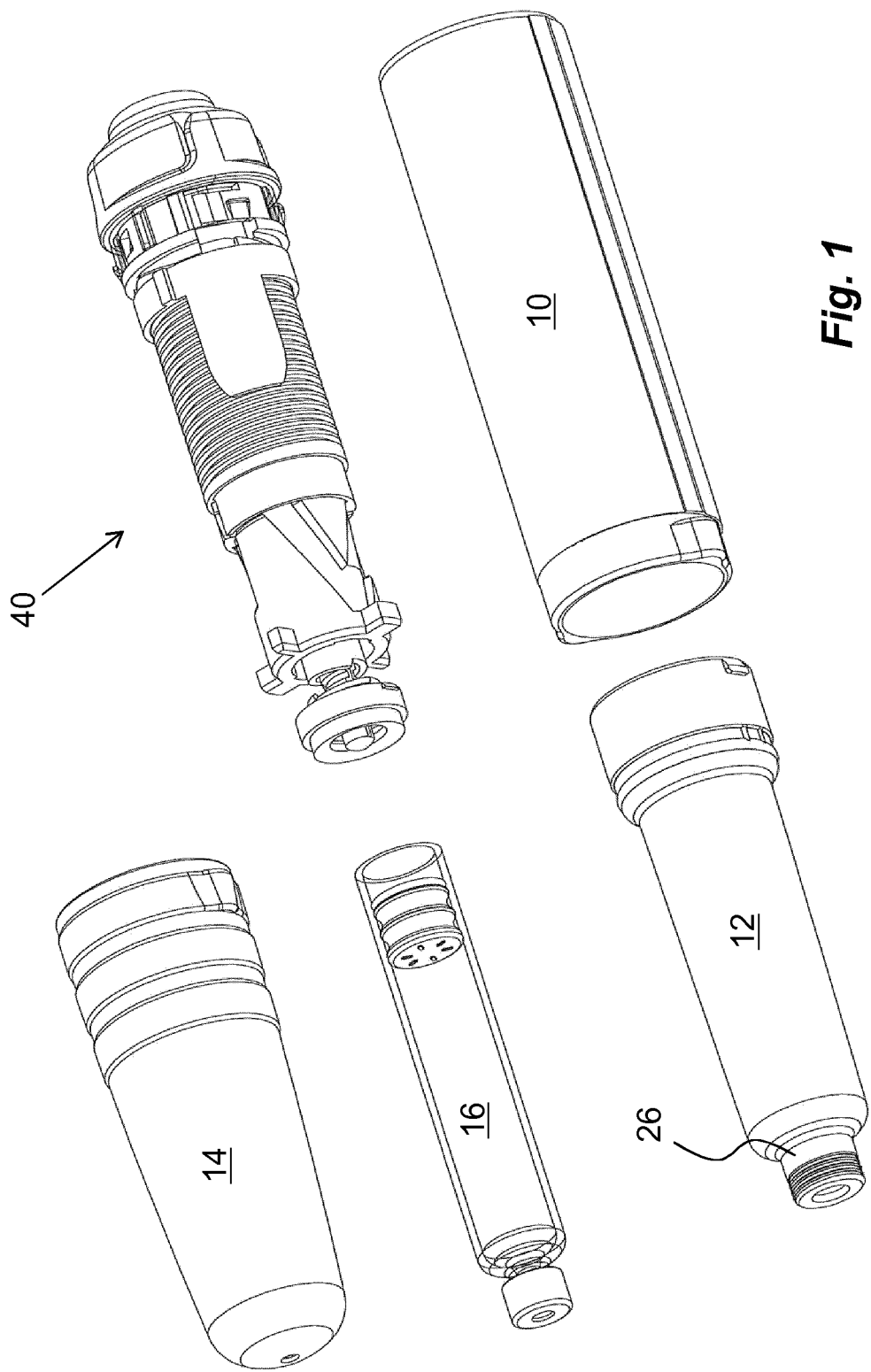
FIG. 1 is an exploded view of a medicament delivery device comprising a drive mechanism according to the present invention.

In the embodiment shown in the drawings, the medicament delivery device comprises a generally tubular distal housing part 10 and a generally tubular proximal housing part 12. In this regard it is to be understood that the housing may comprise a number of different sub-parts depending on manufacturing and assembly aspects. The proximal end of the distal housing part 10 is arranged with attachment elements such that proximal housing part 12 can be attached. Thereby the distal end of the proximal housing part 12 is arranged with a central passage having a diameter generally corresponding to the diameter of the proximal end of the distal housing part 10 and provided with corresponding attachment elements. In this regard it is to be understood that the attachment elements may have a number of different shapes and functions for attaching the medicament container holder to the housing, such as threads, bayonet couplings, snap-in protrusions etc., if the proximal housing part 12 is to be releasably attached to the distal housing part 10. If the proximal housing part 12 is to be permanently attached, the attachment elements may comprise wedge-shaped grip protrusions and recesses that allow assembly but prevent disassembly, welding, glue, etc. A protective cap 14 is also provided for releasably covering the proximal housing part 12.

The proximal housing part 12 is designed as a medicament container holder and is arranged to house a generally tubular elongated medicament container 16, which is provided with a resilient movable stopper 18. The proximal housing part 12 is provided with openings or windows 20 so that the medicament container 16 and its content may be viewed. The proximal end of the medicament container 16 is provided with a neck portion 22 arranged with a penetrable septum 24, FIG. 2. The neck portion 22 is arranged to fit into a neck portion 26 of the proximal housing part 12. The neck portion 26 of the proximal housing part 12 is provided with attachment elements for a medicament delivery member that may be an injection needle provided with a hub having corresponding attachment elements. In this regard the attachment elements may be threads, bayonet couplings, snap-in attachments, luer-connections, just to mention a few options. Further, a generally ring-shaped medicament container fastener 30 is arranged to abut a distally directed surface of a medicament container 16 placed in the proximal housing part 12 with a proximally directed surface. The medicament container fastener 30 is urged in the proximal direction by a compression spring 31 arranged between the medicament container fastener 30 and a proximally directed surface of an end wall 32 of the distal housing part 10. The movement in the proximal direction of the medicament container fastener 30 is limited by radially outwardly directed protrusions 34 on an outer surface of the medicament container fastener 30 cooperating with cut-outs 36 of proximally directed ledges 38 on the proximally directed surface of the end wall 32, FIG. 4a.

Figure 4B:
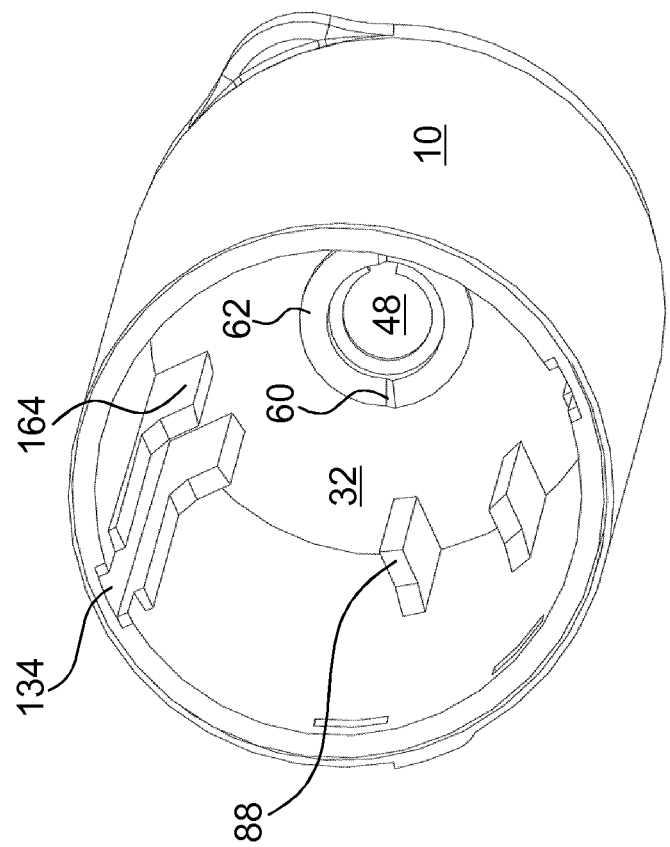
Figure 5:
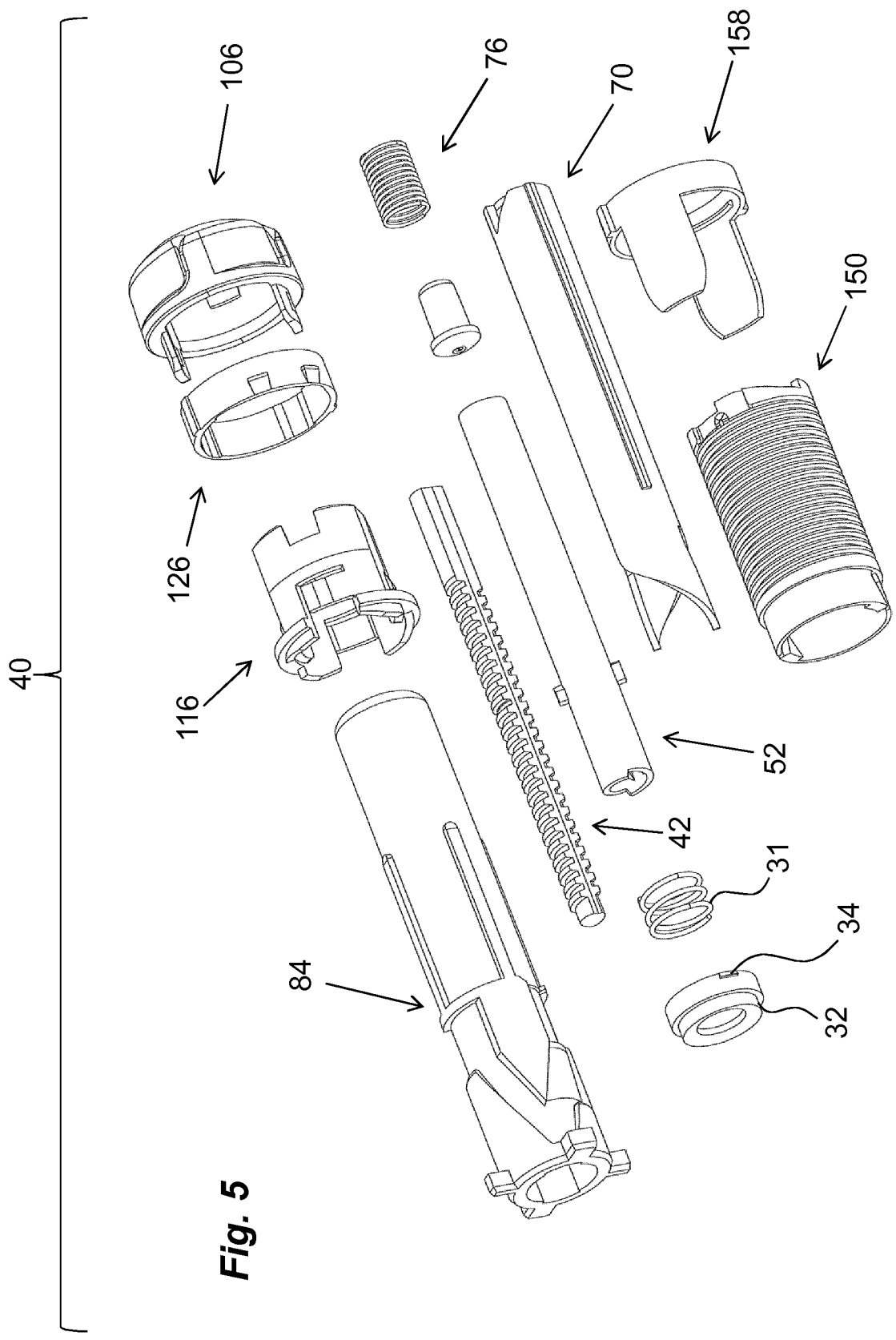
FIG. 5 is an exploded view of a drive mechanism according to the present invention.
Figure 6:
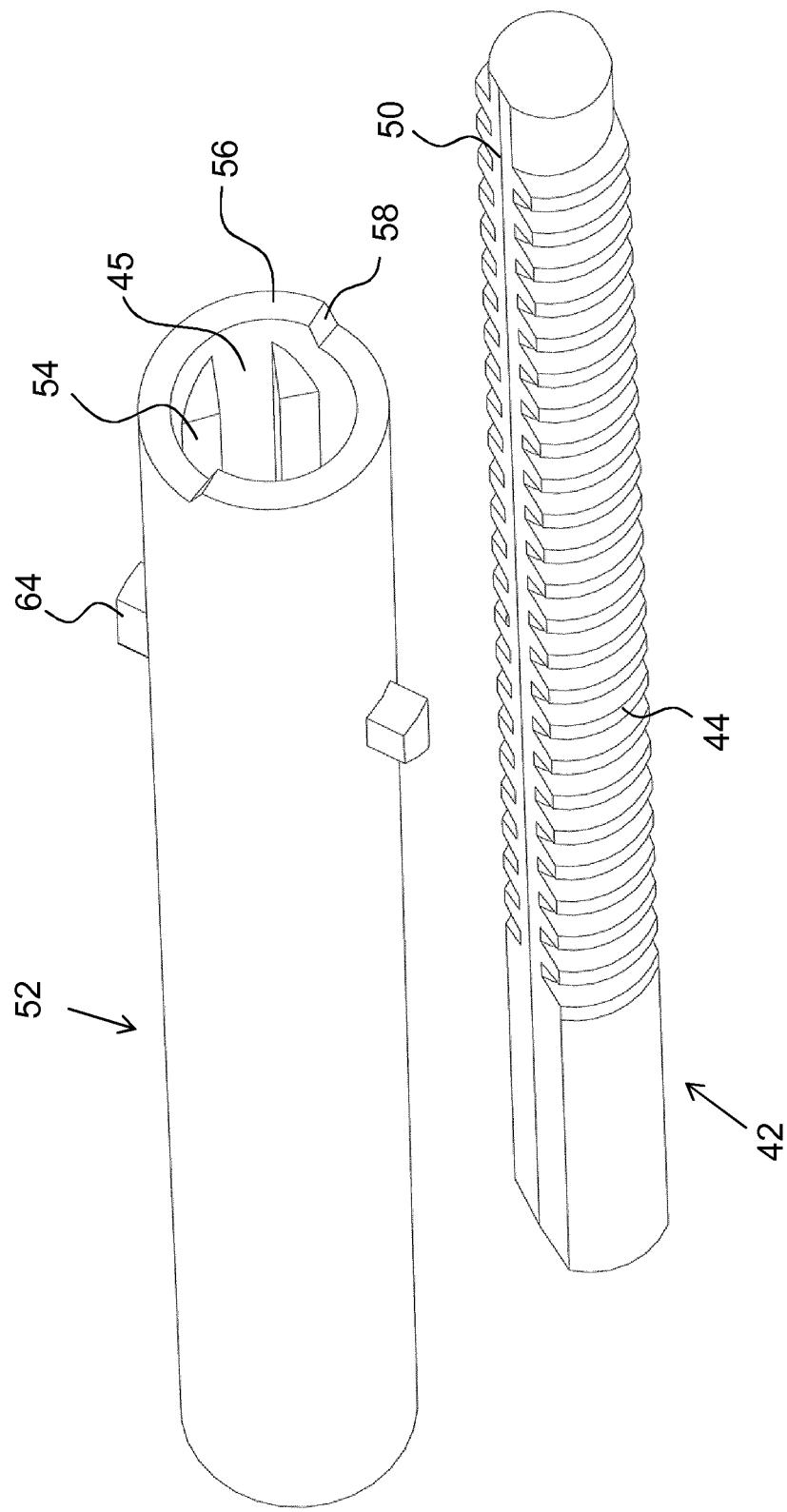

The medicament delivery device further comprises an actuation mechanism 40, FIGS. 1 and 5. The actuation mechanism 40 comprises an elongated plunger rod 42, FIGS. 5 and 6, provided with threads 44 on its outer surface, which threads 44 are arranged to cooperate with corresponding thread segments 46 in a central passage 48 in the proximal end wall 32 of the distal housing part 10, FIG. 4b. The plunger rod 42 is arranged with two longitudinally cut-away sections 50, FIG. 6, on opposite sides of the plunger rod 42, forming support surfaces. The plunger rod 42 is arranged to fit into a generally tubular driver 52. The inner surface of the driver 52 is arranged with two sets of longitudinally extending ledges 54 wherein the plunger rod 42 fits into the space 45 between these sets of ledges 54 such that the support surfaces of the cut-away sections 50 of the plunger rod 42 will be in contact with side surfaces of the ledges 54, whereby the plunger rod 42 is rotationally locked to the driver 52 but linearly movable in the longitudinal direction. The proximal end of the driver 52 is provided with ramped slanted surfaces 56 that end in ledges 58, which ledges 58 interact with ledges 60 on ramped slanted surfaces 62 on a distally directed surface of the end wall 32 of the distal housing part 10 surrounding the threaded central passage 48. The slanted surfaces 56, 60 and the ledges 58, 60 form second audio generating elements as will be described.

Figure 3:
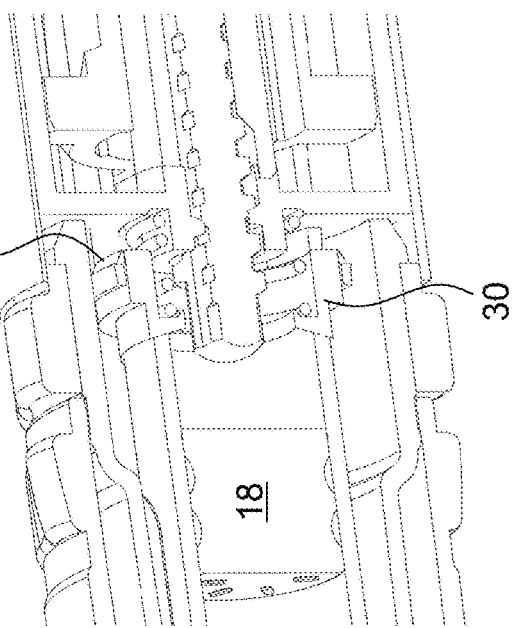
FIG. 3 is a detailed view of a medicament container fastener of the device of FIG. 1, FIGS. 4a-4b, 6-10 are detailed views of components comprised in the medicament delivery device of FIG. 1.
Figure 7:
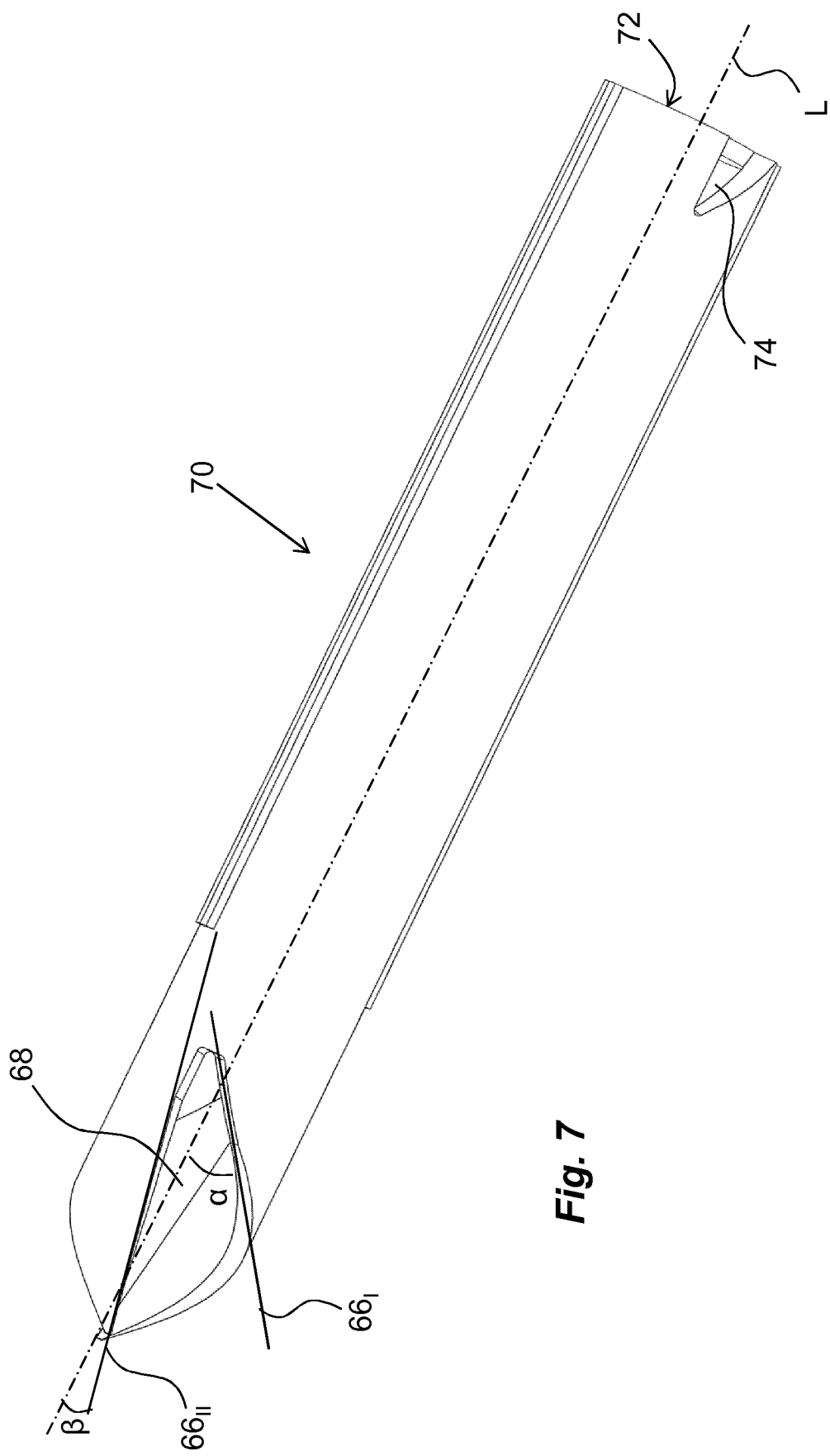

The outer surface of the driver 52 is further arranged with two outwardly directed protrusions 64 arranged on opposite sides of the driver 52, FIG. 6. These protrusions 64 are arranged to interact with edge surfaces 66 of cut-outs 68 at a proximal part of a generally tubular toggle sleeve 70, FIG. 7, which is positioned coaxial and outside the driver 52. The edge surfaces 66 of the toggle sleeve 70 have a certain configuration as seen in FIG. 7, having a first section $66_I$ with an inclination alpha. The first section $66_I$ is then interrupted by a second section $66_{II}$ with a very steep inclination beta and in an opposite direction as the first section $66_I$. The second section $66_{II}$ then ends in a further first section $66_I$. The first and second sections are arranged twice around the proximal end of the toggle sleeve 70. The function of the protrusions 64 and the edge surfaces 66 will be described in detail below. The toggle sleeve 70 is further arranged with an end wall 72 at its distal end and wedge-shaped cut-outs 74 on a distal end area of the toggle sleeve 70, the function of which will be described below. A compression spring 76, hereafter named toggle sleeve spring, FIGS. 3 and 5, is arranged with a distal end in contact with a proximal surface of the end wall 72 of the toggle sleeve 70, and with a proximal end in contact with distally directed surface of an annular flange 78 of a generally tubular washer 80, wherein the washer body extends into the toggle sleeve spring 76. A proximally directed surface of the flange 78 of the washer 80 is in contact with a distal end surface 82 of the driver 52.

Figure 8:
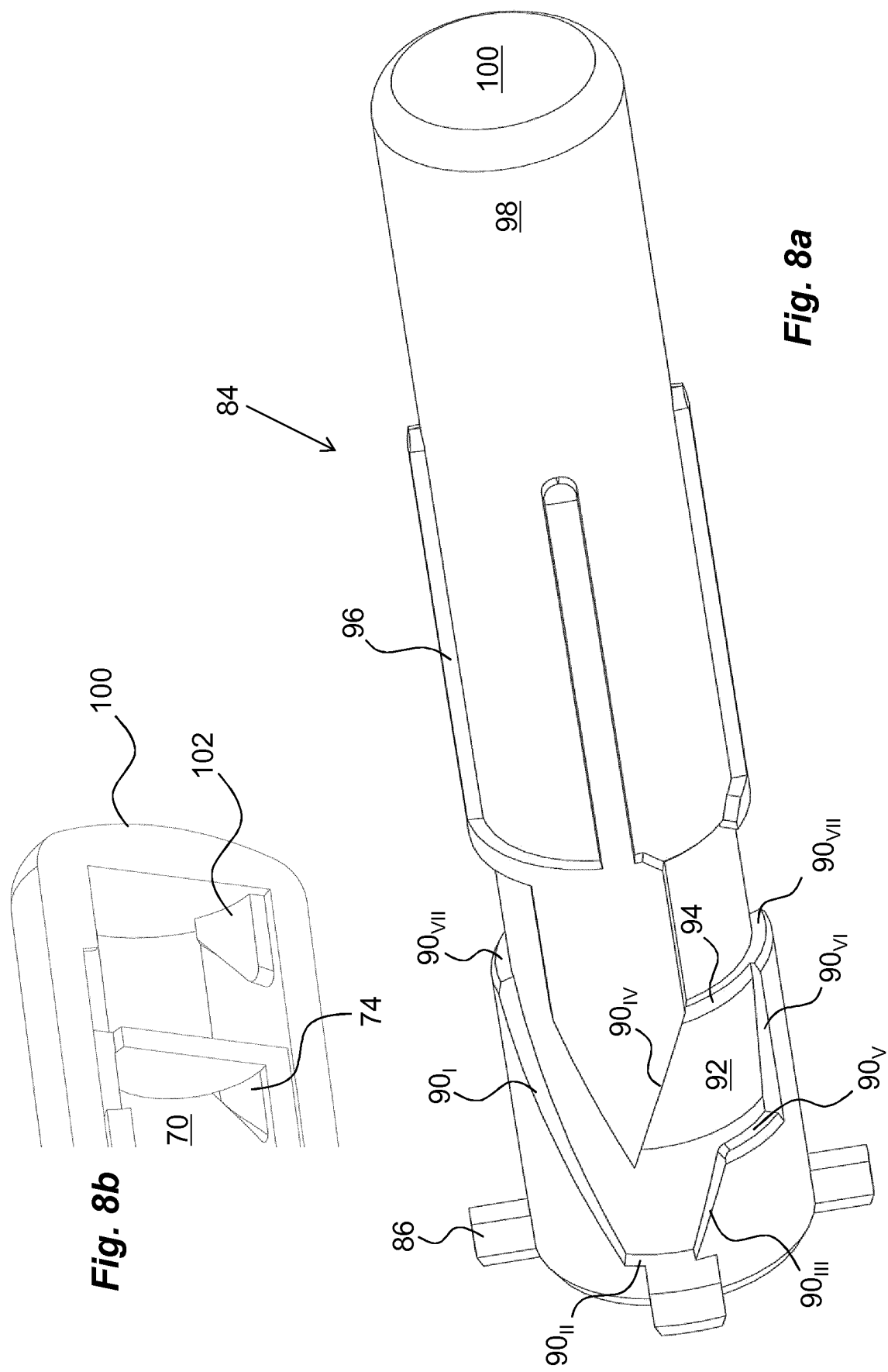

Coaxial with and outside of the toggle sleeve 70 is a generally tubular actuator 84, FIG. 8a. The actuator 84 is arranged with a number of radially outwardly directed ledges 86 at a proximal part thereof, which ledges 86 are configured to fit in between pairs of longitudinally extending ledges 88, FIG. 4b, on an inner surface of the distal housing part 10, thereby creating a rotational lock between the actuator 84 and the distal housing part 10 but allowing axial movement of the actuator 84. The actuator 84 is further arranged with a number of sets of ledges 90 on its outer surface, which ledges 90 have a certain extension as will be explained. A first section $90_I$ of the ledges is arranged facing the distal direction and with a steep inclination in relation to the longitudinal direction of the actuator 84. At one end of the first section, a second section $90_{II}$ is arranged, extending in the circumferential direction. A third section $90_{III}$ is connected to the second section $90_{II}$, extending with an inclination in relation to the longitudinal direction L. Parallel to the third section $90_{III}$, a fourth section $90_{IV}$ is placed, thus having an inclination in relation to the longitudinal direction L.

A fifth section $90_V$ then connects to the fourth section $90_{IV}$, extending in the circumferential direction. The fifth section $90_V$ then connects to a sixth section $90_{VI}$ extending in the longitudinal direction. The sixth section $90_{VI}$ then connects to a seventh section $90_{VII}$ extending in the circumferential direction, which in turn connects to the first section of a subsequent set of sections 90. A surface area between the fourth section $90_{IV}$ and the sixth section $90_{VI}$ is arranged as a wedge-shaped slanted ramp or surface area 92 having a distally directed ledge 94. The sets of ledges are repeated two times around the circumference of the actuator 84. Distally of the ledges 90 are a number of longitudinally extending ledges 96 placed. The distal end part 98 of the actuator 84 is arranged with a somewhat dome-shaped end wall 100 wherein the distal end part 98 of the actuator 84 is arranged to protrude out of the distal end of the medicament delivery device and to act as a push button part for a user, as will be described. A proximal surface of the end wall 100 is further arranged with proximally directed wedge-shaped protrusions 102, which protrusions 102 are arranged to cooperate with the wedge-shaped cut-outs 74 on the toggle sleeve 70, FIG. 8b.

Figure 9:
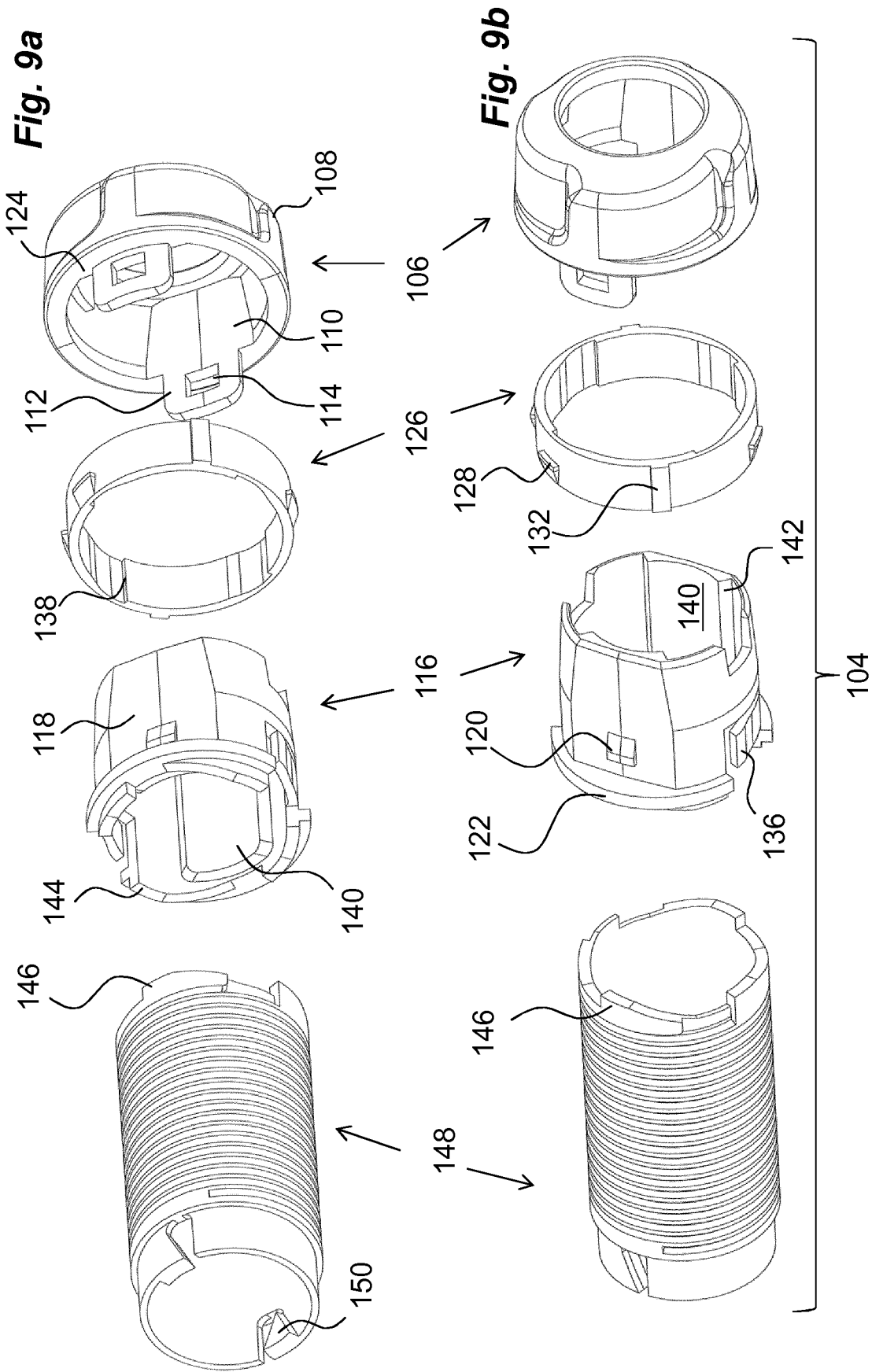

At the distal end of the housing a generally tubular activator 104 is arranged, FIG. 9. It has a distal grip part 106 that when connected to the distal housing part 10 is placed distally of the distal housing part 10 and having a diameter somewhat larger than the diameter of the distal housing part 10. The side surfaces of the grip part 106 may be arranged with grip elements, such as longitudinally extending ridges 108. The grip part 106 is further arranged with two planar surfaces 110 directed inwards and towards each other in the radial direction. Two proximally directed tongues 112 extend from the planar surfaces 110. The tongues 112 are arranged with cut-outs 114. The grip part 106 is arranged to fit onto a distal area of a generally tubular proximal part 116 of the activator 104 wherein the planar surfaces 110 of the grip part 106 are abutting corresponding planar surfaces 118 of the proximal part 116 that are facing radially outwards. The planar surfaces 118 of the proximal part 116 are arranged with wedge-shaped protrusions 120 that are intended to fit into the cut-outs 114 of the tongues 112 and lock the grip part 106 to the proximal part 116 when the two parts are assembled.

The proximal part 116 of the activator 104 is arranged with an outwardly, circumferentially extending, ledge 122 in a proximal area thereof. Further, the grip part 106 is arranged with a proximally directed edge 124 such that when the grip part 106 is assembled with the proximal part 116, an annular recess is formed between the ledge 122 and the edge 124. A locking ring 126 is positioned rotationally in the recess between the ledge 122 and the grip part 106. The locking ring 126 is arranged with protrusions 128 on its outer surface, which protrusions 128 are arranged to fit into recesses 130, FIG. 4a, on an inner surface of the distal housing part 10. Further, the outer surface of the locking ring 126 is arranged with ledges 132, which ledges 132 fit into longitudinally extending recesses 134 on the inner surface of the distal housing part 10, FIG. 4b. This locks the activator 104 to the distal housing part 10, allowing rotation of the activator 104, as will be described.

Further, the proximal part 116 of the activator 104 is provided with a number of resilient arms 136 that extend in the circumferential direction of the activator 104. The arms 136 have a resiliency in the radial direction. The free ends of the arms 136 of the activator 104 are designed to be in contact with an inner surface of the locking ring 126 so as to cause a frictional resistance so as to avoid unwanted spontaneous movement of the activator 104 if the medicament delivery device for example is shaken. Further, the inner surface of the locking ring 126 is arranged with ledges 138 having surfaces in the circumferential direction, which ledges 138 cooperate with the free ends of the arms 136 so that the activator 104 can only be turned in one direction. Also, the inner surface of the proximal part 116 is arranged with two curved surfaces 140 provided at opposite sides and facing each other, having a curvature generally corresponding to the outer surface of the actuator 84. The curved surfaces are limited in the circumferential direction by longitudinally extending guide ledges 142, the function of which will be described below.

Further, at the proximally directed end surface of the activator 104, a number of proximally directed wedge-shaped protrusions 144 are arranged. These wedge-shaped protrusions 144 are designed to interact with at least one corresponding wedge-shaped protrusion 146 on a distal end surface of a generally tubular activator sleeve 148, which activator sleeve 148 is arranged rotational and slidable inside the distal housing part 10 and coaxial and outside the actuator 84. The inner surface of the activator sleeve 148 is arranged with two inwardly directed protrusions 150 at a proximal area thereof, which protrusions 150 are designed with a number of side surfaces having different inclinations as seen in FIG. 9a. The protrusions 150 are designed to be in contact with and follow the ledges 90 of the actuator 84 as will be described. Adjacent the protrusions 150, cut-outs 151 are provided, enabling some flexing in the radial direction of the protrusions. The protrusions 150 are a part of first audio generating elements as will be described.

Figure 4A:
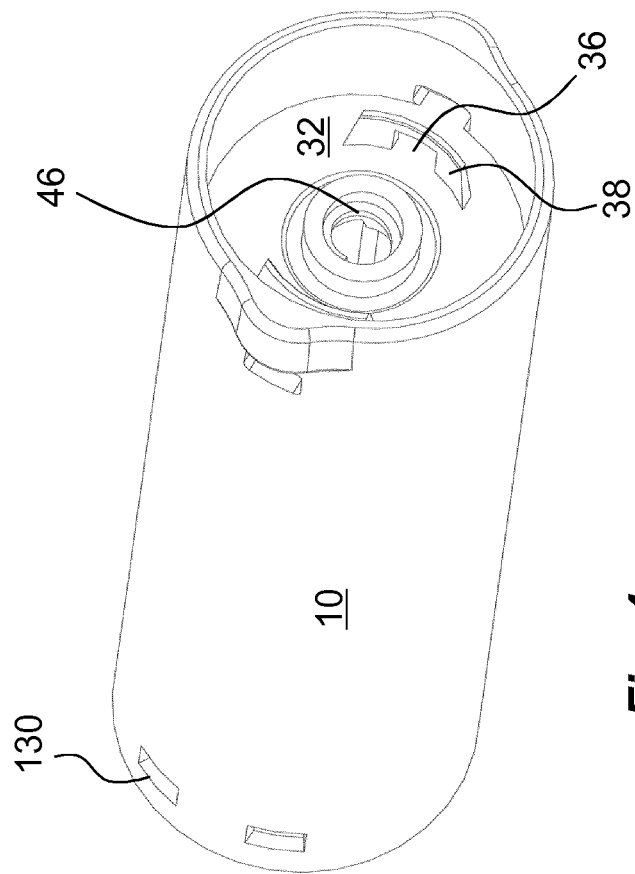
Figure 10:
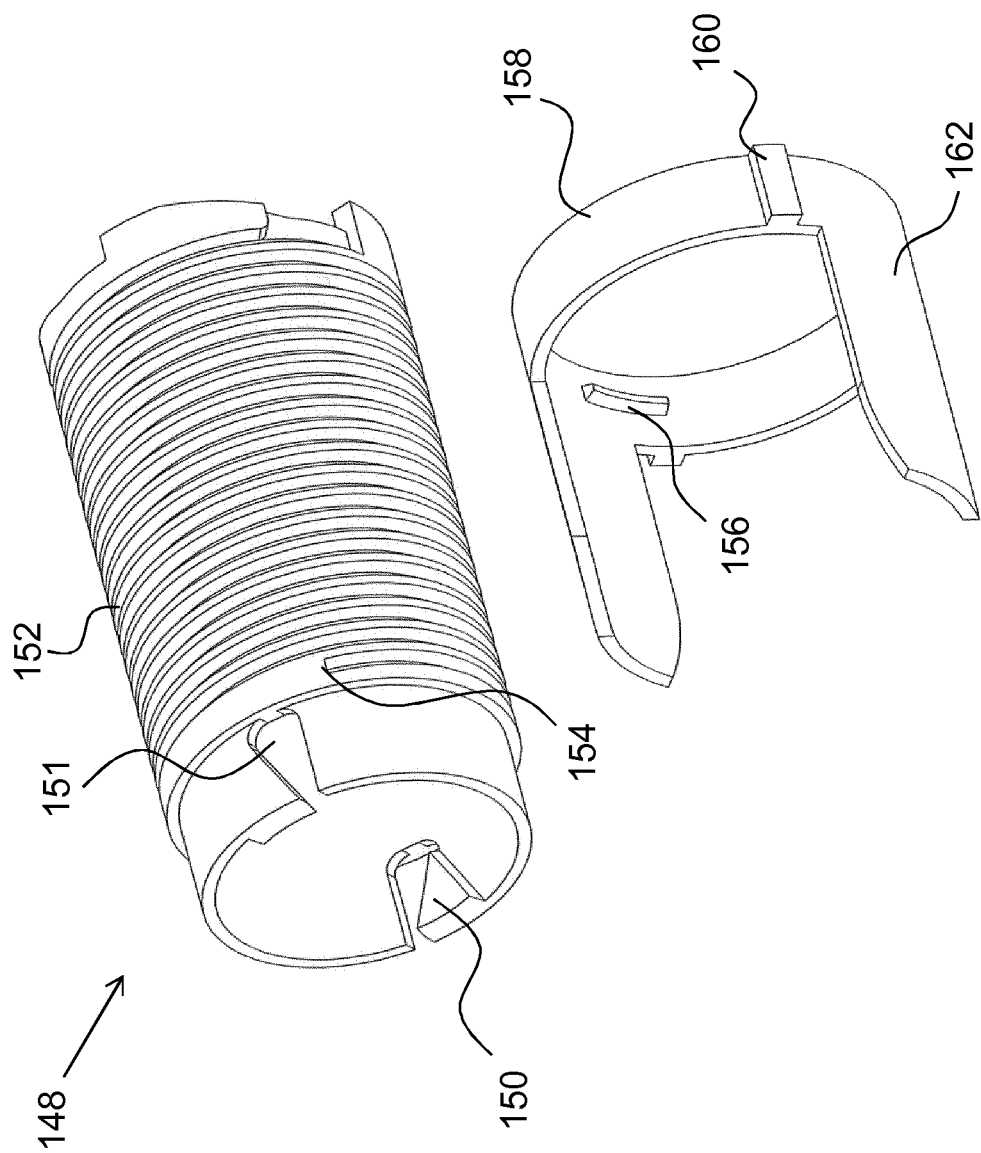

The activator sleeve 148 is further arranged with a spirally extending groove 152 on its outer surface, FIG. 10. The groove 152 has an end wall 154 at the proximal end of the activator sleeve 148. The groove 152 is intended to interact with at least one ledge 156 arranged on an inner surface of a stop ring 158, which stop ring 158 is positioned coaxially outside the activator sleeve 148. The outer surface of the stop ring 158 is arranged with longitudinally extending ledges 160, which ledges 160 are designed to fit into the longitudinally extending recesses 134 on the inner surface of the distal housing part as seen in FIG. 4b. This connection provides a rotational lock of the stop ring 158 while allowing movement in the longitudinal direction. The stop ring 158 is further arranged with proximally directed tongues 162, which tongues 162 are arranged to cooperate with ledges 164 on either side of the recesses 134 for providing guiding stability of the stop ring 158 as will be described.

Figure 2:
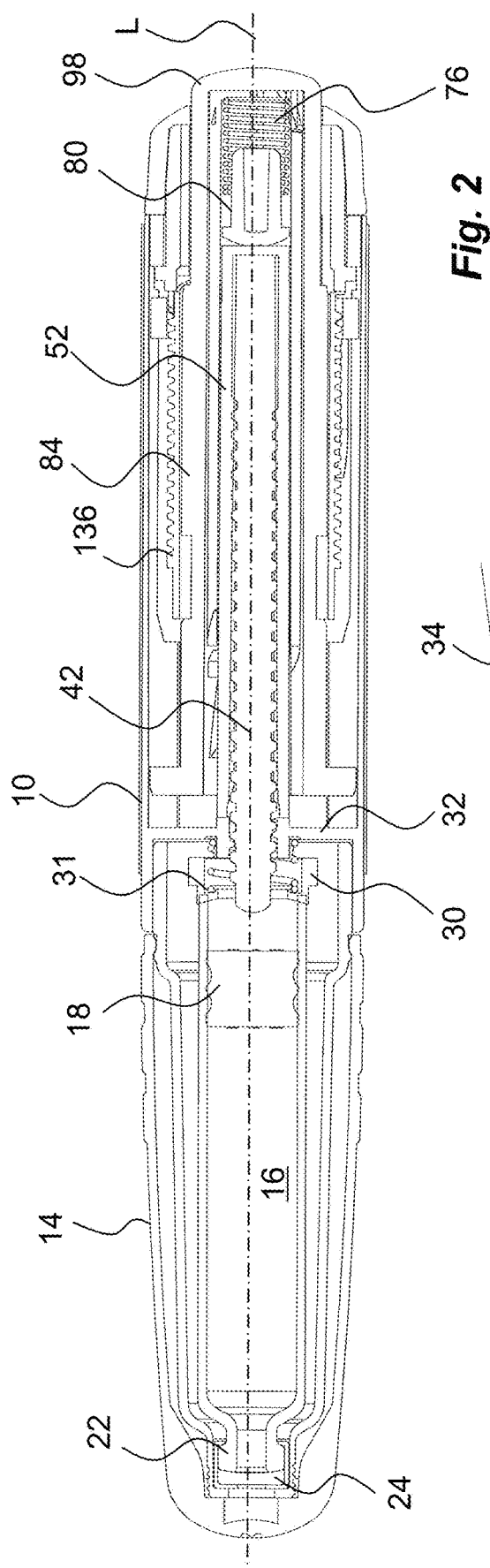
FIG. 2 is a cross-sectional view of the medicament delivery device of FIG. 1.

The invention is intended to function as follows. When the device is delivered to a user, the plunger rod 42 is in its most distal position as shown in FIG. 2. Further the actuator 84 is in its most proximal position, with only a short part of the distal push button part 98 extending through the distal end of the medicament delivery device. The actuator 84 is locked in that position by the protrusions 150 of the activator sleeve 148 being in contact with the distal surface of the ledge $90_{VII}$ of the actuator. This prevents movement of the actuator 84 in the distal direction against the urging force of the toggle sleeve spring 76 that is tensioned between the toggle sleeve 70 and the actuator 84. The activator 104 is in an initial position where the ends of the resilient arms 136 of the proximal part 116 are resting against the ledges 138 of the wedge-shaped protrusions on the inner surface of the locking ring 126.

The medicament delivery device could either be delivered to a user with a medicament container 16 already mounted in the proximal housing part 12 and thus ready to use or be delivered without a medicament container mounted and possibly also with the proximal housing part 12 unconnected to the distal housing part 10, wherein the user has to put a medicament container 16 inside the proximal housing part 12 and then attach the proximal housing part 12 to the distal housing part 10 of the medicament delivery device. The container fastener 30 with the spring 31 is now pressing the medicament container in the proximal direction, thereby reducing the risk of rattling of the medicament container.

In either way, when the medicament delivery device is to be used, the protective cap 14 is removed and a medicament delivery member is attached to the neck portion 26 of the proximal housing part 12. When the medicament delivery member is an injection needle, the attachment causes a distal pointed end of the injection needle to penetrate the septum 24 of the medicament container, thereby causing a flow passage through the needle from the interior of the medicament container 16.

In order to unlock and activate the medicament delivery device, the user turns the grip part 106, which is counter clockwise in the embodiment shown. Any rotation in the opposite direction is prevented by the arms 136 of the proximal part 116 engaging the ledges 138 of the wedge-shaped protrusions of the locking ring 126. In the embodiment shown, there are three ledges 138 of the wedge-shaped protrusions along the inner circumference of the locking ring 126 with thus a 120 degree displacement between the ledges 138, and consequently the activator 104 is turned 120 degrees per step, as will be described in more detail below.

Figure 11:
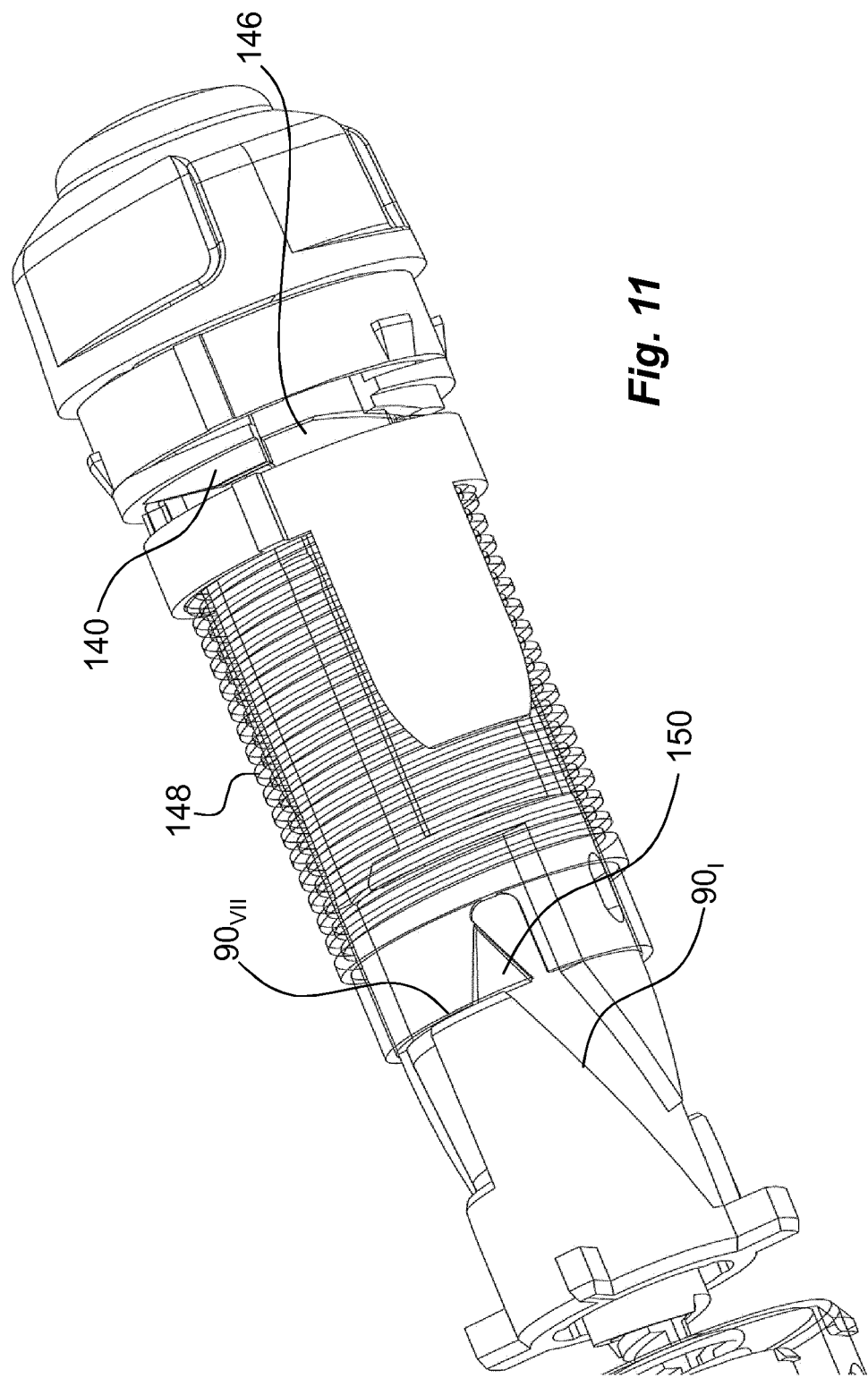

The initial mutual positions of the proximal part 116 and the activator sleeve 148 are shown in FIG. 11. In this position, the at least one wedge-shaped protrusion 144 of the proximal part 116 is in full contact with the space between the protrusions 146 of the activator sleeve 148, causing a rotational lock between the two components. When the grip part 106 with the proximal part 116 is turned, the activator sleeve 148 follows, whereby its protrusions 150 will slide along the ledge $90_{VII}$ of the actuator 84 until the protrusions 150 come to the steep ledge $90_I$, FIG. 11. This will enable the actuator 84 to be moved in the distal direction by the toggle sleeve spring 76 acting between the distal end of the driver 52 and the toggle sleeve 70, which in turn is abutting the distal end surface of the actuator 84, which in turn causes the push button part of the actuator 84 to extend in the distal direction through the distal end of the medicament delivery device. During the turning of the activator sleeve 148, the ledge 156 of the stop ring 158 will slide in the spiral groove 152 of the activator sleeve 148.

Figure 12:
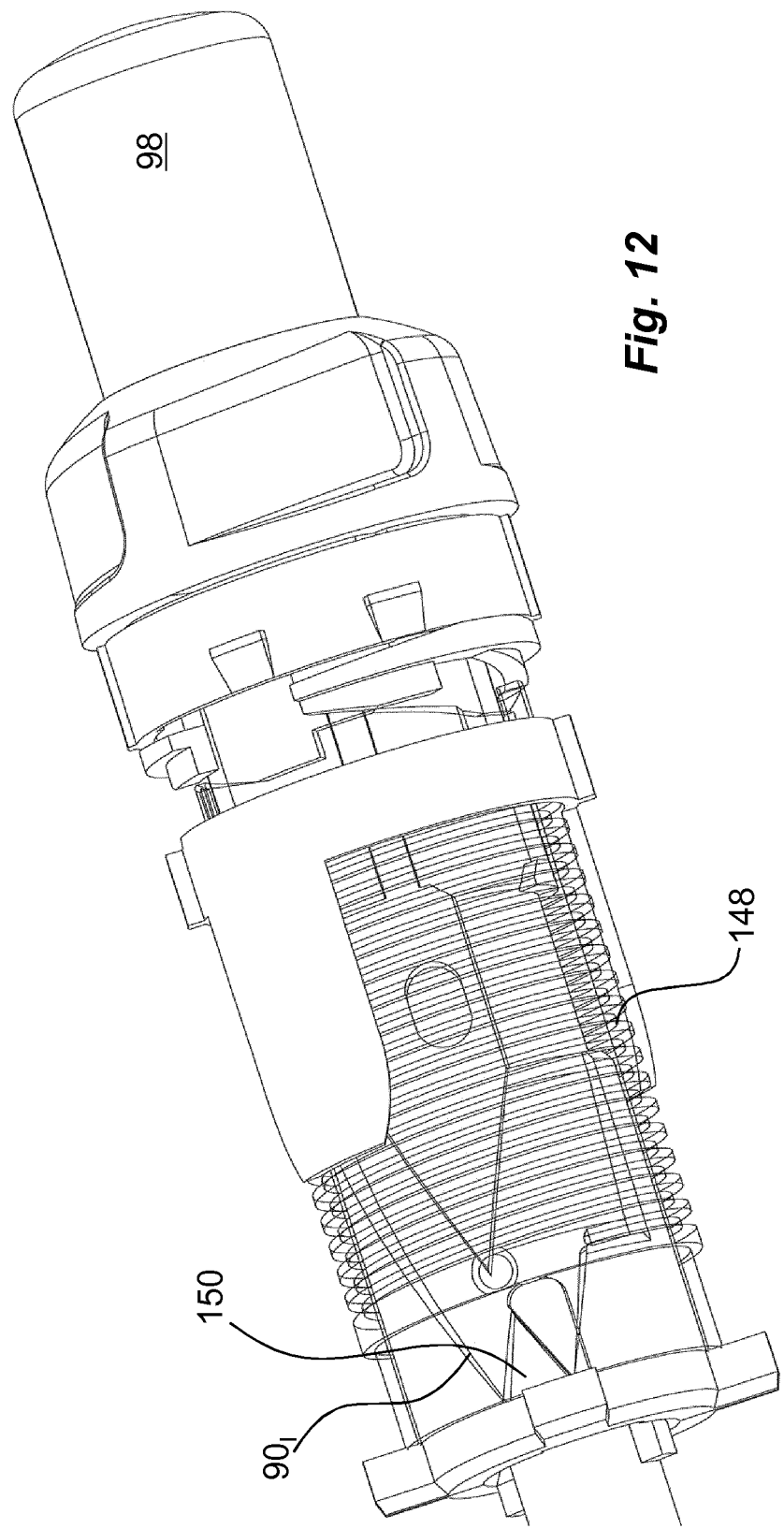

The user now stops turning the activator 104 but since the protrusions 150 of the activator sleeve is in contact with the steep inclined ledge $90_I$ of the actuator 84, the activator sleeve 148 continues to rotate because the actuator 84 is rotationally locked to the housing by the ledges 86 cooperating with the ledges 88 of the distal housing part 10. When now the proximal part 116 is stationary and the activator sleeve 148 is rotating, the inclined surface of the at least one wedge-shaped protrusion 146 of the activator sleeve 148 will cooperate with the inclined surface of the wedge-shaped protrusions 144 of the proximal part 116, whereby the activator sleeve 148 is forced in the proximal direction. The rotation of the activator sleeve 148 is stopped when the protrusions 150 are moved in contact with the circumferential ledge $90_{II}$ of the actuator 84, which stops the movement in the distal direction of the actuator 84, FIG. 12. The push button part 98 of the actuator 84 is protruding out of the distal end of the medicament delivery device as seen in FIG. 12. When the actuator 84 is moved in the distal direction, the ledges 96 on the outer surface of the actuator will be positioned parallel to the guide ledges 142 of the proximal part 116 of the activator 104, thereby preventing any turning of the activator 104.

When the actuator 84 is moving in the distal direction as described above, so is the toggle sleeve 70 since they are in contact with each other because the toggle spring is acting on the toggle sleeve 70, in turn acting on the actuator 84. In the initial position the protrusions 64 of the driver 52 are positioned in the junction between the first and second sections $66_I$ and $66_{II}$ of the edge surfaces 66 as seen in FIG. 13. When now the toggle sleeve is moving in the distal direction together with the actuator the protrusions will slide along the first section $66_I$, FIG. 14, and because it has an inclination β in relation to the longitudinal direction, the toggle sleeve 70 will turn in relation to the driver 52. The driver 52 is prevented from turning in the anti-clockwise direction due to the ledges 58 of the driver 52 cooperating with the ledges 60 of the end wall 32 of the housing. The turning of the toggle sleeve 70 will cause it to move somewhat in the proximal direction in relation to the actuator 84 because of the cooperation between the ramped cut-outs 74 of the toggle sleeve 70 and the wedge-shaped protrusions 102 of the actuator 84, FIG. 15. During continued movement of the toggle sleeve 70 in the distal direction, the protrusions 64 of the driver 52 will come out of contact with the first section $66_I$ whereby the toggle sleeve 70 will be turned back to the initial position because of the cooperation between the ramped cut-outs 74 and the wedge-shaped protrusions 102 as seen in FIG. 16.

Figure 17:
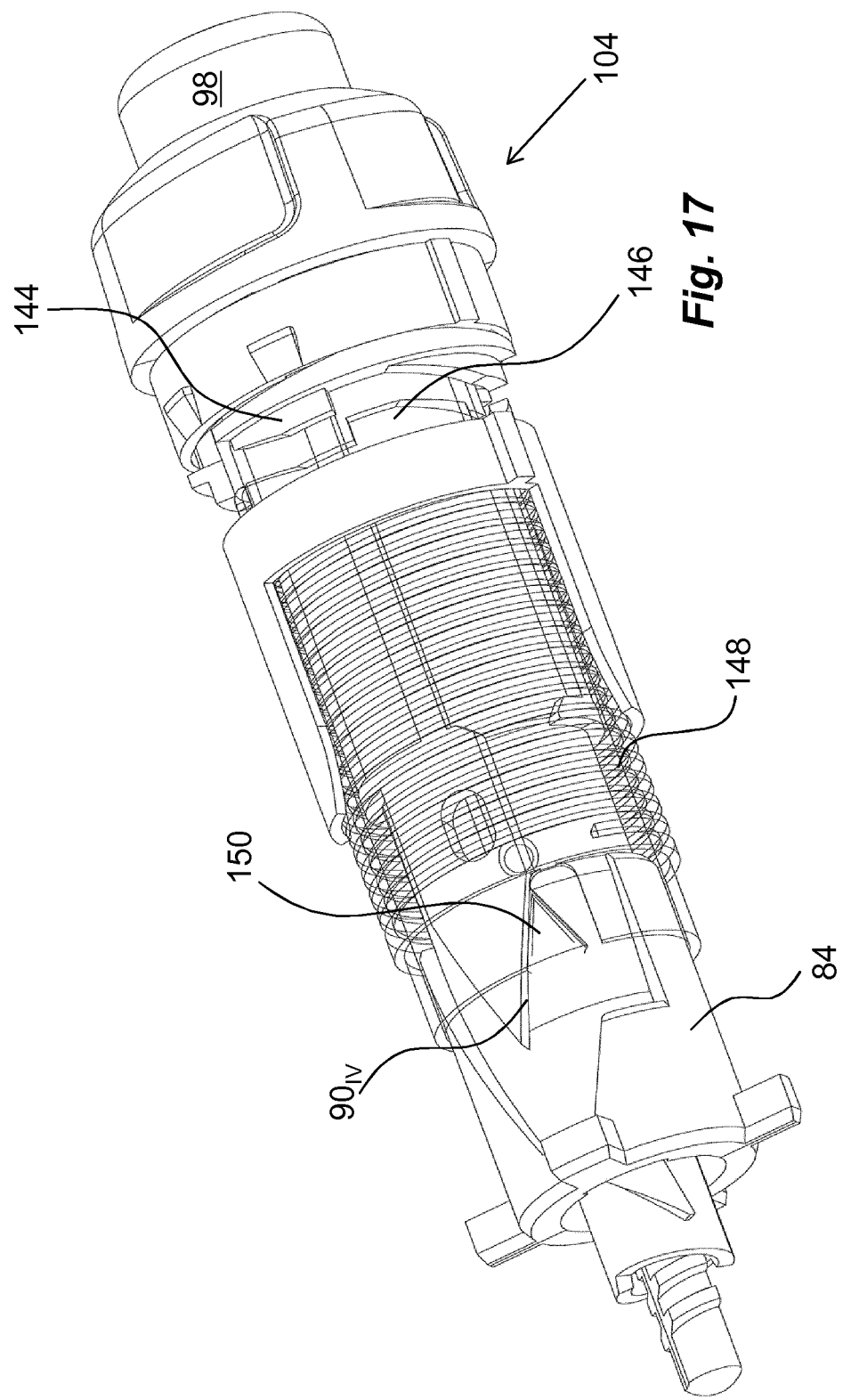

The device is now activated and ready to deliver a dose of medicament. If a medicament delivery member has not been attached before, it may be attached now to the proximal end of the medicament delivery device. The proximal end of the medicament delivery device is now placed at a dose delivery site, and if the medicament delivery member is an injection needle, a penetration is performed at the dose delivery site. The next step is to deliver a dose of medicament. The user then presses on the push button part 98 of the actuator 84 so that it moves in the proximal direction. This will cause the inclined ledge $90_{IV}$ of the actuator 84 to be moved in contact with the protrusions 150 of the activator sleeve 148, FIG. 17. This will in turn move the activator sleeve 148 in the proximal direction whereby the wedge-shaped protrusions of the activator sleeve 148 are moved out of contact with the wedge-shaped protrusions 144 of the proximal part. Any turning of the activator 104 will thus not affect the medicament delivery device. At the same time, the activator sleeve is turned due to the inclination of the ledge $90_{IV}$.

As the actuator 84 is moved in the proximal direction, so is the toggle sleeve 70. This movement will cause the first section $66_I$ of the cut-outs 68 to come in contact with the protrusions 64 of the driver 52, FIG. 18, and continuous movement of the toggle sleeve 70 will cause the protrusions to slide along the inclined first section, FIG. 19, whereby the driver is turned in the clockwise direction. The turning is not obstructed by the ledges of the driver and the end wall of the housing. The turning of the driver 52 will in turn cause a turning of the plunger rod 42 because of the rotational lock between them and since the plunger rod 42 is threadedly connected to the passage 48 of the end wall of the housing 10, the plunger rod 42 will be moved in the proximal direction, FIG. 18, whereby it will act on the stopper 18 for expelling a dose of medicament through the medicament delivery member.

During the movement in the proximal direction of the actuator, the protrusions 150 of the activator sleeve 148 will enter the slanted surface area 92 and at the end of the movement of the actuator 84 pass the ledge 94, causing the actuator 84 to be locked in the depressed position, FIG. 20. The passing of the ledge 94 by the protrusions 150 is facilitated by the flex obtained by the cut-outs 151. Also, the passing of the ledge 94 by the protrusions 150, comprised in the first audio generating elements, will cause an audible signal or a click and maybe also a tactile signal when the protrusion 150 hits the surface of the actuator 84 after the ledge 94. This signal indicates to the user that the dose delivery sequence is terminated and the medicament delivery device can be removed. Further, during the turning of the driver for delivering a dose, the slanted surfaces 56 of the driver 52 will slide on the slanted surfaces 62 surrounding the central passage 48 and at the end of the dose delivery sequence, the ramped surfaces will come to the ledges 58 and 60 causing a sudden movement in the proximal direction of the driver 52, whereby an audible and tactile signal is created when the slanted surfaces 56 and 62 hit each other, wherein these surfaces and ledges are comprised in the second audio generating element. This signal is also information to the user that the dose delivery sequence is terminated and that the medicament delivery device can be removed.

There is further a safety feature, should the user during the pressing of the actuator 84 in the proximal direction suddenly release the actuator 84 before completing the dose delivery sequence. In this case only a part of the amount of medicament has been delivered. The toggle sleeve spring 76 will then try to force the actuator 84 in the distal direction. However, this is prevented in that the protrusion 150 will be moved in contact with the circumferentially extending ledge $90_V$, FIG. 21, thereby preventing further movement. If not stopped, it would otherwise lead to the actuator 84 being again moved to a fully extended position, whereby it would be possible to deliver a new full amount of medicament. This is now prevented by the ledge $90_V$. The user may now press on the partly extending push button part 98 for delivering the remainder of the dose of medicament, after which the actuator 84 is locked as described above.

The medicament delivery device may now be removed from the dose delivery site, the medicament delivery member removed and discarded in a safety container and the protective cap 14 re-connected to the proximal end of the medicament delivery device. The above mentioned sequences of dose setting and dose delivery are repeated until the medicament container 16 is empty and as described above, the ledge 156 of the stop ring 158 is moved a distance along the spiral groove 152 of the activator sleeve 148 for each dose setting operation, whereby the stop ring 158 is moved in the proximal direction. In order to prevent setting a dose that is larger than the remaining dose quantity of the medicament container, the length of the spiral groove 152 around the circumference of the activator sleeve 148 corresponds to the total amount of medicament in the medicament container. Thus, the setting of the last dose may be limited by the ledges 156 of the stop ring 158 abutting the end wall 154 of the groove 152, FIGS. 22 and 23, preventing further turning of the activator 104 and the activator sleeve 148. This means that no dose larger than the remaining amount of the medicament container 16 can be set.

It is to be understood that the embodiment described above and shown in the drawings is to be regarded only as a non-limiting example and that the invention may be modified in many ways within the scope of the patent claims.

The invention claimed is:

1. A medicament delivery device comprising:
    a housing,
    a stop ring rotationally fixed to and longitudinally slidable relative to the housing, and
    an actuation mechanism arranged inside said housing, where the actuation mechanism comprises:
    a plunger rod arranged to act on a stopper of a medicament container;
    an actuator arranged slidable and connected to the plunger rod for acting on the stopper when said actuator is operated by displacing the plunger rod in a longitudinal direction of the actuation mechanism, where the actuator comprises an outside surface defined by a plurality of ledges; and
    an activator rotatably arranged for activating said actuation mechanism and for setting a dose;
    wherein the activator comprises a generally tubular activator sleeve having an outside surface threadedly engaged with the stop ring such that rotation of the activator causes the stop ring to move axially relative to the housing,
    wherein the activator sleeve is arranged coaxial and outside of the actuator, where the activator sleeve comprises an inner surface having radially inward directed protrusions having side surfaces of different inclinations that contact and follow the plurality of ledges on the outside surface of the actuator such that said activator sleeve is rotated when said actuator is operated, wherein a first audio generating mechanism comprises audio generating elements and said protrusions on the inner surface of the activator sleeve, where the protrusions flex radially outward when cooperating with said audio generating elements and then flexes back inward for generating an audible signal after an operation for delivering the dose.

2. The medicament delivery device according to claim 1, wherein said first audio generating mechanism comprises surface areas on which said protrusions slide during rotation of said activator sleeve, wherein the surface areas are arranged with distally directed ledges of the plurality of ledges causing sudden impact of said protrusions.

3. The medicament delivery device according to claim 2, wherein said surface areas are slanted and terminate in the distally directed ledges of the plurality of ledges.

4. The medicament delivery device according to claim 3, wherein the distally directed ledges of the plurality of ledges also functions as locking elements so as to lock said actuator after the operation for delivering the dose.

5. The medicament delivery device according to claim 4, wherein said actuator is arranged with inclined ledges of the plurality of ledges cooperating with said protrusions, wherein the inclined ledges of the plurality of ledges are arranged inclined in relation to a longitudinal axis.

6. The medicament delivery device according to claim 5, wherein the distally directed ledges of the plurality of ledges are interconnected with the inclined ledges of the plurality of ledges such that turning of said activator sleeve moves said protrusions from a locking position to a release position of said actuator.

7. The medicament delivery device according to claim 1, further comprising a toggle sleeve operably arranged between said actuator and said plunger rod for urging the plunger rod in a proximal direction during operation of said actuator, wherein said plunger rod is arranged with threads, a driver non-rotatably connected to said plunger rod, wherein the driver is arranged with protrusions on its outer surface, that said toggle sleeve is arranged with surfaces inclined in relation to a longitudinal axis, causing a rotation of said driver and said plunger rod when said actuator and said toggle sleeve are moved in the proximal direction, further comprising a second audio generating mechanism comprising audio generating elements arranged between said driver and a component fixed in relation to said housing.

8. The medicament delivery device according to claim 7, wherein said second audio generating elements comprises slanting surfaces arranged both on a proximal end of the driver and on an end wall of the housing, where engagement and relative rotation of the slanting surfaces will cause an audible signal when a dose delivery sequence is terminated.

* * * * *